United States Patent
Denecke (12)

(10) Patent No.: US 6,232,350 B1
(45) Date of Patent: May 15, 2001

(54) PREPARATION AND METHOD FOR THE TREATMENT AND PREVENTION OF DIMENTIA DISORDERS

(75) Inventor: Rainer Denecke, Hamburg (DE)

(73) Assignee: Altramed Holdings, Ltd., Hamilton (BE)

(*) Notice: Subject to any disclaimer, the term of this patent is extended or adjusted under 35 U.S.C. 154(b) by 0 days.

(21) Appl. No.: 08/852,274

(22) Filed: May 7, 1997

Related U.S. Application Data

(63) Continuation-in-part of application No. 08/532,681, filed as application No. PCT/DE94/00366 on Mar. 30, 1994, now abandoned.

(30) Foreign Application Priority Data

Apr. 10, 1993 (DE) ................................................. 43 11 870

(51) Int. Cl.⁷ .................................................. A61K 31/135
(52) U.S. Cl. ........................... 514/648; 514/428; 514/874
(58) Field of Search ..................... 514/648, 874, 514/428

(56) References Cited

U.S. PATENT DOCUMENTS

| | | | |
|---|---|---|---|
| 5,047,431 | * 9/1991 | Schickaneder et al. | |
| 5,455,275 | * 10/1995 | Fontana | 514/648 |
| 5,470,883 | * 11/1995 | Stromberg | 514/648 |
| 5,491,173 | * 2/1996 | Toivola et al. | 514/648 |
| 5,589,500 | * 12/1996 | Edwards et al. | 514/648 |
| 5,605,700 | * 2/1997 | DeGregorio et al. | 514/648 |
| 5,719,191 | * 2/1998 | Maclean et al. | 514/648 |

OTHER PUBLICATIONS

IRCS Medical Science: Clinical Medicine, vol. 4, No. 3, G. Delitala et al., "Pituitary–Gonadal Response To Clomiphene Citrate In Parkinsonism", (1976), p. 113.*

International Journal of Geriatric Psychiatry, vol. 2: 125–126, J.J. Oram et al, "Treatment of Senile Dementia With Thyrotrophin Releasing Hormone and Clomiphene", (1987).*

Progress in Neuro–Psychopharmacology, vol. 4, J. Libiger et al, "Drug Induced Dementia", Sep. 1980.*

Van Den Koedijk et al, "Comparative Affinity of Steroidal And Non–Steroidal Antioestrogens, Cholesterol Derivatives and Compounds With A Dialkylamino Side Chain For The Rat Liver Antioestrogen Binding Site", *Biochemical Pharmacology*, vol. 43, No. 12, pp. 2511–2518, 1992.*

*Journal of the National Cancer Institute*, vol. 85, No. 14, Jul. 21, 1993, p. 1111.*

* cited by examiner

Primary Examiner—Keith D. MacMillan
(74) Attorney, Agent, or Firm—Harness, Dickey & Pierce, P.L.C.

(57) ABSTRACT

A preparation for the treatment and/or prevention of dementia disorders, especially disorders due to regressive cellular changes. A close of at least one steroidal antagonist is included as the active agent. A mixture of such substances can also be applied.

17 Claims, 1 Drawing Sheet

PREPARATION AND METHOD FOR THE TREATMENT AND PREVENTION OF DIMENTIA DISORDERS

CROSS-REFERENCE TO RELATED APPLICATION

This patent application is a continuation-in-part of patent application Ser. No. 08/532,681, filed Dec. 8, 1995 now abandoned, which is incorporated by reference herein, which is a national stage filing of PCT application No. PCT/DE94/00366, filed Mar. 30, 1994 which claims priority to German application No. P4311870.4, filed Apr. 10, 1993.

BACKGROUND AND SUMMARY OF THE INVENTION

The present invention relates to a preparation for the treatment and prevention of dementia disorders, particularly disorders caused by regressive cellular changes.

The appearance of such disorders becomes more likely with increased age. The consequence of this is that, given an increasing life expectancy and a resulting growing proportion of older people among the population, the prevalence of dementia disorders caused by old age is constantly increasing. Manifestations of aging in connection with the central nervous system are accompanied by a multitude of structural and functional alterations. These include, for example, cerebral shrinkage and loss of brain weight, nerve-cell degenerations, various amyloid formation, and lesions of the cerebral vessel-connective tissue apparatus.

The above-named alterations affect above all persons who, in the wider sense, are afflicted with Alzheimer's disease. This means for one thing that when Alzheimer's disease is present, the above-named alterations occur in a particularly strong way, and, for another thing, that the above-mentioned alterations can reinforce the symptoms of Alzheimer's disease or encourage the appearance of these. Lesions of the cerebral vessel-connective tissue apparatus are, for example, the causes of Multi-Infarct Dementia (MID). At present, vigorous debate is still going on about the causes of Multiple Sclerosis (MS).

Parkinson's Disease can be mentioned as another neurological affliction. This disorder appears together with a pronounced dopamine deficiency in the region of the substantia nigra and in the corpus striatum. The cause of this disorder is a degeneration of dopaminergic projection neurons in the substantia nigra and corpus striatum. In this disorder, symptoms of dementia have also been described.

In addition to the already-mentioned dementia disorders, a large number of other general degeneration disorders can also occur, such as "impaired brain function of old age" (IBFO). The probability that strokes will occur likewise becomes greater with increasing age. Furthermore, diseases based on arteriosclerotic vessel changes can also be mentioned.

Another effect that occurs more with an increasing process of aging is a decrease in the adaptability of the "stress management system." This endogenous system for managing stress is located at the sites of the hypothalamus-hypophysis-adrenal glands. The mechanism of action of this stress management system is based essentially on the fact that when injuries, infections, or psychosocial stress occur, for example, the human body reacts by releasing a large number of mediators, which act with one another in a finely balanced way to restore homeostasis.

These mediators ensure, among other things, that any increased cell activity is again reduced, so as to prevent a prolonged overstraining of the cells that could lead to cellular damage and, in the extreme case, to the dying-off of cells.

Examples of such mediators are the steroid hormones. These hormones bind specifically to receptors, which are disposed in the region of the cellular nucleus. This binding to receptors induces a broad spectrum of metabolic processes. Moreover, a series of neuro-endocrino-immunological interactivities also occur, which provide security for the integrity and the health of the affected individual.

Until now, no preparation has been known that has only mild side effects but can prevent the occurrence of manifestations of degeneration caused by old age, or in the case of a disorder that has already appeared, can counteract the further progression of the disorder or can treat the disorder.

Therefore, an object of the present invention is to specify a preparation of the initially-named type which will have a high efficacy in the treatment and prevention of dementia disorders while producing only mild side effects.

This object is attained in accordance with the invention by administering a drug that contains at least one steroidal antagonist as the active agent.

BRIEF DESCRIPTION OF THE DRAWING

The present invention will be more fully understood by reference to the following detailed description of the preferred embodiment of the present invention when read in conjunction with the accompanying drawing in which.

DESCRIPTION OF THE PREFERRED EMBODIMENT

Figure 1:
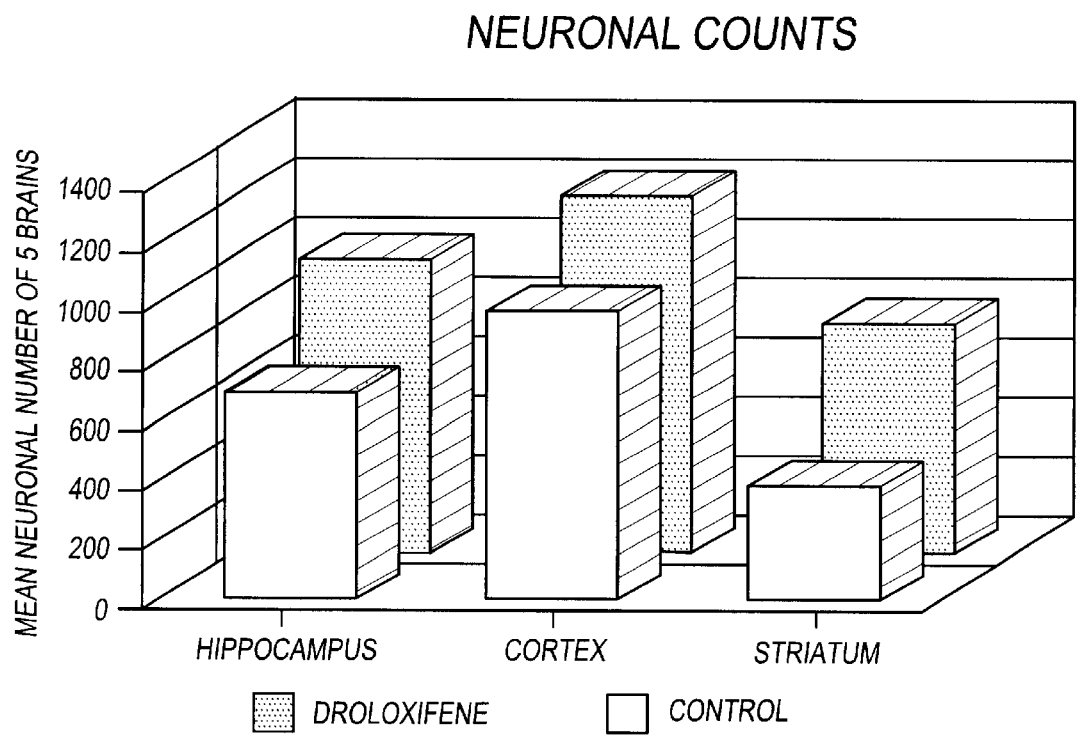
FIG. 1 is a table which illustrates the counts of neutrons with nucleoli depicted for three different brain regions investigated.

By introducing steroidal antagonists as cell-nucleus receptor blockers or as modulators in the steroid-receptor superfamily, mechanisms are activated that induce interactive connections between apparently unrelated systems. Because of this induction process, it is possible to achieve stimulating effects on an aged or altered neuroendocrine system. The result of this fact is the possibility of modulating and treating nervous-system lesions.

For example, either pure or partial steroidal antagonists or agonists can be used. One of the partial steroidal antagonists, for example, is tamoxifen. In addition, tamoxifen has an inhibiting influence on L- and N-type $Ca^{2+}$ channels. By way of such calcium antagonism, overly high intracellular $Ca^{2+}$ channels. By way of such calcium antagonism, overly high intracellular $Ca^{2+}$ levels can be avoided that might have resulted in cellular death. This means that tamoxifen has a neuroprotective action.

Moreover, an influence by tamoxifen on $Ca^{2+}$-activated $K^+$ channels can also be established. With respect to these channels there are indications that they can be expected to exert an influence on learning and memory functions. A ligand such as tamoxifen, which acts on both channel types, can thus have an immediate positive influence on learning and memory functions and have a long-term antidegenerative action. Thus with such a substance we have an ideal agent for use against Alzheimer's dementia. This principle of action of tamoxifen can also be found with other steroidal antagonists. It is known of antiestrogens that they have anti-oxidant properties. They reduce membrane fluidity and thus stabilize cell membranes against lipid peroxidation.

Thus the basic effect of antiestrogens results both from the fact that they are ligands for $Ca^{2+}$ and $K^+$ channels, and also from the fact that they have anti-oxidant properties. From this a protective and/or a therapeutic effect can be inferred.

With respect to the already-mentioned steroidal antagonists, a distinction should be made between pure antagonists and those that are partial agonists. A pure agonist has no intrinsic antagonistic properties and is suited to a specific receptor. Antagonists that act in part as agonists are receptor-nonspecific in at least one region of their spectrum of applications and can display differing effects depending on the type of receptor. Thus their action is regionally dependent on which organ or which part of the body the action is displayed. Furthermore, the metabolites of the above-mentioned substances can also be used. One special class of the steroidal antagonists are the antiandrogens, which likewise can have pure or partial properties and whose metabolites can be used as well.

Another sub-group of the steroidal antagonists is the antiestrogens, which likewise can be invested with a pure or partial spectrum of properties, and the metabolites and derivatives associated with these. Centrally acting aromatase inhibitors are members of the group of functional estrogen antagonists.

A large number of suitable steroidal antagonists is described in the publication "Comparative Affinity of Steroidal and Nonsteroidal Antiestrogens, Cholesterol Derivatives and Compounds with a Dialkylamino Side Chain for the Rat Liver Antiestrogen Binding Site," Biochemical Pharmacology, Vol. 43, No. 12, pp. 2511–2518, 1992, C.D.M.A. van den Koedijk, C. Vis van Heemst, G. M. Eisendoorn, J. H. H. Thijssen, and M. A. Blankenstein. Here, in particular, the triphenylethylene antiestrogens and the non-triphenylethylene antiestrogens should be emphasized. Such substances are in particular tamoxifen, 4-OH-tamoxifen, 3-OH-tamoxifen, N-desmethyl tamoxifen, monophenol tamoxifen, cyanotamoxifen, toremifene, 4-OH-toremifene, N-desmethyl toremifene, monophenol toremifene, deaminotoremifene, nafoxidine, zindoxifene, trioxifene, keoxifene, CB 7432; ICI 164,384; D 18954; ZK 119.010; D 15414; LS 3360; LS 3348; LS 3347; ORG 31710; ORG 31376.

A preferred species of compositions which can be used for the treatment and prevention of dementia disorders are tamoxifen, tamoxifen derivatives and similar pharmaceutical compositions. A special summarization of these compositions are the triphenylethylene antiestrogens with more than one side chain.

In particular, it is possible to use triphenylethylene antiestrogens and derivatives with the following structural formulas. The meaning of R1, R2, R3, and R4 is defined in the following table.

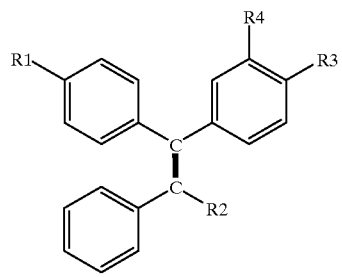

| Compound | R1 | R2 | R3/R4* | RBA |
|---|---|---|---|---|
| Tamoxifen | —O—$(CH_2)_2$—N—$(CH_3)_2$ | —$CH_2CH_3$ | | 100 |
| 4-OH-Tamoxifen | —O—$(CH_2)_2$—N—$(CH_3)_2$ | —$CH_2CH_3$ | R3 = —OH | 24 |
| 3-OH-Tamoxifen | —O—$(CH_2)_2$—N—$(CH_3)_2$ | —$CH_2CH_3$ | R4 = —OH | 30 |
| N-Desmethyltamoxifen | —O—$(CH_2)_2$—NH—$CH_3$ | —$CH_2CH_3$ | | 9 |
| Monophenoltamoxifen | —OH | —$CH_2CH_3$ | | 0.2 |
| Cyanotamoxifen | —O—$(CH_2)_2$—N—$(CH_3)_2$ | —C≡N | | 3 |
| CB 7432 | —O—$(CH_2)_2$—N⟨pyrrolidine⟩ | —$CH_2CH_3$ | R3 = —I | 140 |
| Toremifene | —O—$(CH_2)_2$—N—$(CH_3)_2$ | —$CH_2CH_2$—Cl | | 48 |
| 4-OH-Toremifene | —O—$(CH_2)_2$—N—$(CH_3)_3$ | —$CH_2CH_2$—Cl | R3 = —OH | 27 |
| N-Desmethyltoremifene | —O—$(CH_2)_2$—NH—$CH_3$ | —$CH_2CH_2$—Cl | | 9 |
| Monophenoltoremifene | —OH | —$CH_3CH_2$—Cl | | <0.1 |
| Deaminotoremifene | —O—$(CH_2)_3$—OH | —$CH_2CH_2$—Cl | | <0.1 |

*Where not indicated otherwise R = —H.

Additionally, it is also possible to use the following non-triphenylethylene antiestrogens.

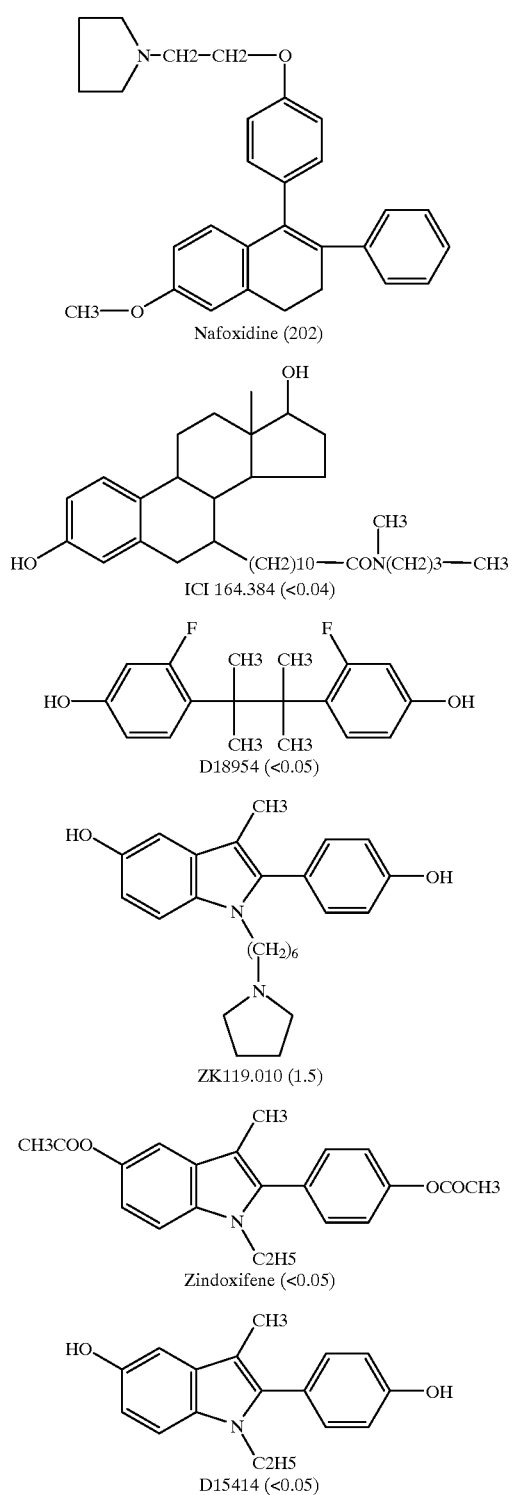

Another class of possible compositions are compounds with a dialkyl amino side chain as defined in the following structural formulas.

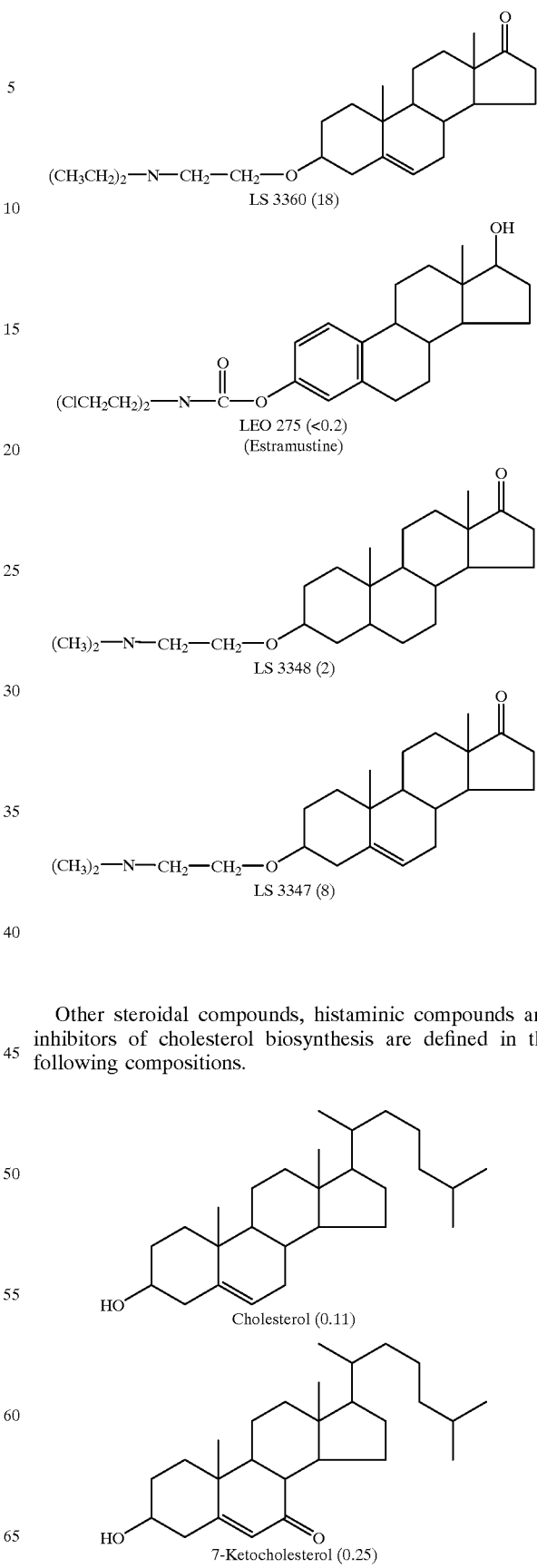

Other steroidal compounds, histaminic compounds and inhibitors of cholesterol biosynthesis are defined in the following compositions.

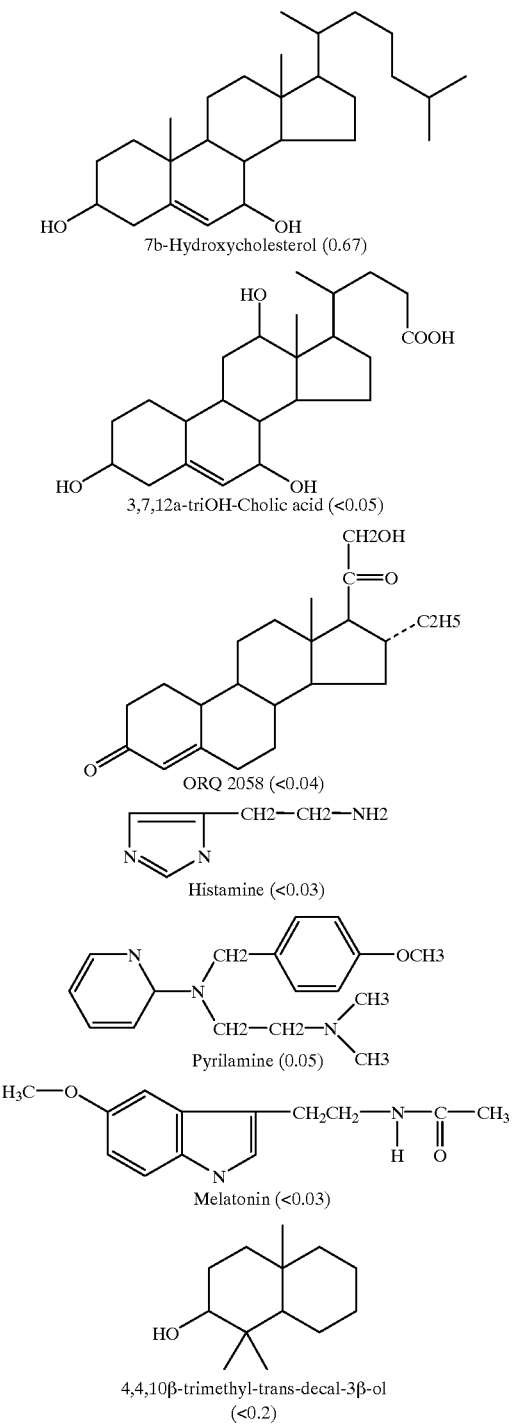

Aside from the previously described steroidal antagonists, steroidal agonist can also be used alternatively or supplementarily, which in turn can have the form of pure agonists or partial antagonists. Moreover, the use of androgens, estrogens, or progesterones is also possible, in each case with a pure or partial profile of activity and with the inclusion of their metabolites.

In terms of the immediate action of the preparation, first an interaction takes place with the receptors, which results in a change in cellular activity and moreover liberates cell substances that encourage a detaching of the ligand from the receptor. After a corresponding detachment, the ligand is broken down with the framework of normal metabolism. Thus, for the maintaining or revival of the effect it is necessary to administer a new dose of the preparation at specific time intervals.

LABORATORY INVESTIGATION AND FINDINGS

To prove the pharmaceutical effect of the proposed preparations with regard to the treatment and prevention of dementia disorders the following morphological study was undertaken to analyze the test results using droloxifene. The following results show the action of droloxifene in the rat brain. There are particularly shown the morphological differences between the brains of droloxifene-treated Fisher rats and untreated control rats.

Structural and functional changes have been observed in central neuron populations of mammals during normal aging. Histological studies have revealed degenerative change sin certain groups of neurons at both the neuritic and cell body level, as well as in the cerebral vasculature. These morphological alterations are considered to be markers of an overall reduction of neuronal function and might lead to the development of Alzheimer's Disease.

At the present time, there is ample debate on the location, extend and relevance of neuronal cell loss and degeneration, respectively, in the aged brain. In order to analyze and characterize age-related and test substance-induced changes in the CNS of rats, routine histomorphological procedures were applied in the study.

Thus, the histological comparison of control versus tamoxifen-treated rate brains will provide the basis for the interpretation of putative neuroprotective effects of this breast cancer antagonist. Morphological alterations which are usually encountered in normal brain aging are also being described for a better evaluation of the different data.

Materials and Methods

Five control and five Droloxifene-treated (10 mg/kg per day for 6 months) female Fischer rats were used in the study. Droloxifene is another name for 3-OH-Tamoxifen. The rats were 16 months old at the beginning of the study and were held at the IBR Company, Walsrode. They had access to food and water ad libitum and were housed in conventional cages under standard laboratory conditions.

After deep anesthesia with 6% sodium pentobarbital, a transcardiac perfusion was performed using heparinized saline as a prerinse, followed by 4% neutral-buffered formalin as fixative. The brains were rapidly dissected out, postfixed and stored in the same fixative.

Coronal sections of the brains were prepared at three defined levels, embedded in paraffin, cut with a microtome knife at 6 micrometers, mounted on gelatine-coated slides and stained with hematoxylin/eosin (H/E) for routine histological evaluation. All blocks were treated in the same way to avoid any differential tissue shrinkage due to processing. The ventral surface of the brain has specific landmarks that are useful for uniform trimming prior to processing. Five brain regions were selected for cell counting: Frontal, parietal, entorhinal cortex, hippocampus and the striatum. To achieve this, the first cut was made at the level of the optic chiasma. This section included the frontal and parietal cortex and striatum. The second cut was just posterior of the mammillary body. This histological section especially included the hippocampus with its CA pyramidal cells. The third cut was made approximately in the middle of the transverse fibers of the pons to pick up the lateral entorhinal cortex.

Neighboring sections were also stained for cresyl violet and luxol-fast-blue to visualize the general cytoarchitecture of the respective brain areas and for cell counting.

Sections of the two groups were matched in order to obtain a high morphological similarity for all five regions under investigation, which is a prerequisite for the comparison of the two groups. Nissi-positive neurons were counted bilaterally in every mounted section at 400× using an ocular grid 10×10. The number of neurons from the two sides of the brain were simply added for each subject. The number of adjacent visual fields investigated was dependent on the respective brain region.

To avoid inaccurate quantification of neurons due to staining variabilities or a plane of sectioning of tissue specimens, counting of relevant cells was based solely on the presence of a nucleolus.

Since no estimation of a total cell population was attempted, no correction factory was used, assuming the same range of error in the counts for both groups.

Results

1. Qualitative Changes in Routine Histology (H/E)

None of the rats showed gross pathological lesion-like tumors, hydrocephalus, infarctions, etc. Routine histological evaluation revealed several age-related changes of brain morphology. One regressive lesion encountered in all of the control rats, and in none of the treated rats, was a multifocal mineralization of the meninges between the hemispheres.

The deposits were found extracellularly without signs of inflammatory reaction. Other parts of the brain were not affected. A progressive change found in all animals was diagnosed as glial cell hyperplasia or gliosis of the cortex, especially in terms of satellitosis around the neurons. This finding was not subject to morphometric analysis. The increase of glial cells was estimated between 20–30%.

Marked differences were observed in cerebral vascular morphology between the two groups. Small arterioles in treated rats very often displayed thicker vascular walls with a prominent, folded intima compared to the control rats. The boundary between the media and the thin intima is indicated by a good visible and rather thick elastic membrane, the internal elastic lamina.

The contraction of this lamina during the fixation procedure accounts for the observed foldings of the whole intima into the luminal space of the bessel. Tissue shrinkage also affects the basement membrane and its endothelial cells, which in that way become very prominent. In contrast, many walls of arterioles in control rats seemed to have more or less lost their elasticity. They showed a rigid appearance and endothelium was hardly visible. A non-folded elastic lamina was present in many cases, but the media seemed to be thinned and structurally homogenized. These phenomena indicated limited shrinkage ability of the tissue during the fixation and embedding process. The underlying morphological substrate for this altered functional behavior could not be definitely established at the light microscopic level, although sometimes hyalinization of the vascular wall could be detected.

Many postcapillary venules had thinner walls and exhibited more prominent endothelial nuclei in a cross-section when compared to control animals.

Here again, vascular walls appeared to be focally hyalinized and rigid with the thickening of endothelial cell processes and without a tendency for shrinkage as seen in treated rats.

At the light microscopic level, there were no differences detected between control and treated rats concerning the capillary and vein vascular walls.

Many pyramidal cells of the hippocampus of Droloxifene-treated rats displayed two or sometimes three nucleoli. The 22-month control rats had significantly fewer neurons with multiple nucleoli, as the single and large nucleoli prevailed. When multiple nucleoli were detected, they were usually smaller than single ones. Multiple nucleoli are thought to be present when cells display an increased production of ribosomes and RNA.

Because most nucleoli were large and single in the controls, nucleolar fusion is likely to take place, rather than disintegration of one or more of the nucleoli in the course of aging.

2. Neuronal Counts And Statistical Analysis

1. Data were summarized per animal for statistical evaluation. The method used was one-way analysis of variance. As there was only a comparison between two groups, the p-value of the F-test is an indicator for group differences. Based on a significance level of $a=0.05$, group differences were not found.

2. Taking into account the variance within one animal, evaluation was performed using hierarchical analyses. The F-value was calculated from the mean squares group/mean squares animal in a group.

With respect to FIGURE 1, a table is shown which depicts the counts of neurons with nucleoli for three different brain regions investigated. Numbers of neurons were not statistically different across the two groups, although in the striatum of control rats a tendency towards decreased cell numbers was evident.

Discussion

A variety of reports on neurophysiological "pathology" within the aged rodent have been presented. However, a great deal of discrepancies exist concerning the type and extend of normal age-related changes. The appearance of these controversies in the literature may result form different strains, sec, and genotype of rats examined, the environment in which the rats were raised, or the age of the rats. In studies describing age-related alterations, rats from 16–36 months of age were evaluated and compared. Thus, it is not surprising that parameters showed no change in one study and were decreased or increased in another. Moreover, it should be kept in mind that age-related "pathology" does not occur unanimously in all, but only in some animals. The degree and quality of alterations are also highly variable and individually different.

These potentially confounding factors could be mostly overcome by studying a well-defined population of rats. Thus, this study contributes to defining certain solely age-related alterations in female Fischer rats at the light microscopic level, and describes the improvement of certain histological parameters in different brain areas after a 6-month Droloxifene (3-OH-Tamoxifen) administration regiment.

1. Routine Histology

Moderate gliosis, as a constant morphological finding during aging, is generally accompanied by functional hyperactivity. A 10–30% increase in astrocyte volume has been found in healthy humans and laboratory rodents (Landfield et al., 1978). It is nuclear if the astrocytic hyperactivity is caused by neurodegenerative events, since the onset of glial hyperplasia can be seen already in middle-age rodents with no evidence of neurodegeneration (Finch, C. E., and Morgan, D. G. 1990).

An overall reduction of neuronal functioning during aging, e.g., neurochemical alterations, might lead to reactive glial cell proliferations. It has been reported that changes of the microvasculature in the aged CNS resulted in decreased nutrient availability of the neurons, and that neuron-to-astrocyte-to-endothelial cell signaling mechanisms initiated compensatory adaptations (Newman et al., 1984).

Thus, it can be assumed that metabolic support for decreased neuronal activity is brought about by glial cells, explaining the observed hyperplasia of this cell type in the present study.

It has been reported that electron microscopic lesions mainly consisted of capillary fibrosis and basement membrane thickenings, probably as a result of disturbed collagen metabolism. Basement membrane thickening and related vascular amyloid-like deposits could constitute the morphological substrate for the observed hyalinization in many postcapillary venules and small arterioles predominantly in the control group. Moreover, the detected rigidity and firm structure of the vascular wall at the light microscopic level is attributable to a decreased amount of elastic fibers and a concomitant replacement by or transformation/degration into collagenous fibrils. Taken together, cerebral vascular sclerosis and related aberrations are obviously features commonly encountered in rats of this strain and age, and there is clear evidence that Droloxifene is a compound able to ameliorate these pathological conditions.

Multiple small foci of basophilic mineral deposits were found exclusively in the meninges predominantly between the frontal cortices. They were almost always associated with thin-walled blood vessels and displayed a more or less visible internal lamination. This is a well-known age-related regressive change in rodents, although the fact that none of the tested rats was affected is an unusual finding which lacks an explanation as of yet. Dietary factors are though to play an important role in the formation of cerebral mineralization.

2. Quantitative Analysis of Nissi-Stained Neurons

Quantification of neurons in the brains of men and animals have been performed by many investigators with conflicting results. With the method used in this study, a statistically significant cell loss in aged rats could not be observed in the areas investigated. However, a tendency to reduced neuron numbers was obvious for the striatum of control rats.

Several reports indicated that CNS neurons showed various degrees of atrophy with advancing age, i.e., a decreased of perikaryal volume and shrinkage of the nucleus/nucleolus by morphological means. This atrophy would result in decreased cell counts in a given section when the above-described nucleoli-method is applied. Thus, it seems likely that the putative neuron loss in the striatum is overestimated and that neurons may still be present, but just reduce din size. This should be borne in mind when considering the present controversies about neuron losses during aging. Neuron atrophy is compatible with neuron survival, and does not immediately precede neuron death. Cell atrophy thus might have been prevented by Droloxifene.

Cell counting in the striatum should be put forward on a broader base, i.e., sampling procedure should be dramatically extended in order to get statistically more relevant data. These features are valuable parameters in assessing a putative neuroprotective effect of triphenylethylene derivatives used in adjuvant breast cancer therapies. The histological results point to an overall improvement of senescence-related alterations under this specific pharmacotherapy.

PREFERRED DOSAGE AND ADMINISTRATION

The recommended dosage of the selected antiestrogen for treatment of dementia disorders in humans according to the present invention is between 5–100 mg/day, with a range of between 20–60 mg/day being the preferred range. The typical expected dose will be about 40 mg/day, with this value being variable up or down depending upon the body mass of the patient. Administration should be conducted for a period of between 3 and 24 months, with the preferred period being between 6 and 12 months. These dosages and the suggested periods of treatment are recommendations only and may be modified according to clinical results as necessary so that they are either greater or lesser in order to maximize the effectiveness of the treatment.

EXAMPLE OF THE PRESENT INVENTION

The following Example represents a preferred embodiment of the present invention. The following regiment is illustrative and is not intended to be limiting, the scope of the invention being fully defined by the appended claims. According to a preferred regimen, a male human having a body mass of between 72 and 78 kg is treated with droloxifene with a dosage of 40 mg/day administered once per day for a period of six months.

While the present invention has been described in connection with different embodiments thereof, it will be understood that it is capable of further modifications and this application is intended to cover any variations, uses, or adaptations of the invention following, in general, the principles of the invention and including such departures from the present disclosure as come within known or customary practice in the art to which the invention pertains, and as may be applied to the essential features hereinbefore set forth and as fall within the scope of the invention or the limits of the appended claims.

Having thus described my invention, what I claim is:

1. A method of treating dementia in a human patient, the method including the steps of:

forming a pharmaceutical composition containing an antiestrogenically effective amount of an antiestrogen, said antiestrogen having a structure according to the formula

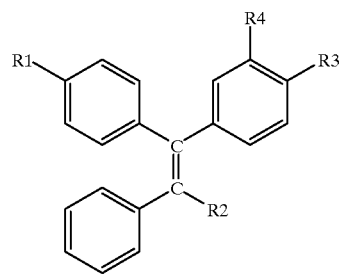

wherein $R_1$ is selected from the group consisting of

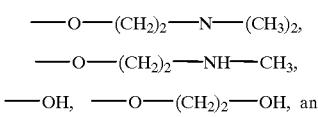

-continued

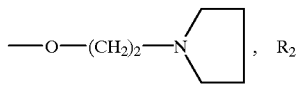

being selected from the group consisting of —CH$_2$—CH$_3$, —C≡N, and —CH$_2$ CH$_2$—Cl, and the remaining R-groups being selected from the group consisting of —H, —OH or —I; and administering an amount of said pharmaceutical composition to the human patient in sufficient quantity so as to be effective in the treatment of dementia.

2. The method of treating dementia according to claim 1, wherein said composition is administered to the human patient in an amount of about between 5 and 100 mg per day.

3. The method of treating dementia according to claim 1, wherein said composition is administered to the human patient in an amount of about between 20 and 60 mg per day.

4. The method of treating dementia according to claim 1, wherein said composition is administered to the human patient in an amount of about 40 mg per day.

5. The method of treating dementia according to claim 1, wherein the period for administration is between about 3 months and 24 months.

6. A method of treating dementia in a human patient, the method including the steps of:

forming a pharmaceutical composition containing an antiestrogenically effective amount of an antiestrogen, said antiestrogen being selected from the group consisting of tamoxifen or a tamoxifen derivative, said tamoxifen derivative being selected from the group consisting of 4-OH-tamoxifen, 3-OH-tamoxifen, N-desmethyltamoxifen, monophenoltamoxifen, cyanotamoxifen, CB 7432, toremifene, 4-OH-toremifene, N-desmethyltoremifene, monophenoltoremifene, and deaminotoremifene; and administering an amount of said pharmaceutical composition to the human patient in sufficient quantity so as to be effective in the treatment of dementia.

7. The method of treating dementia according to claim 6, wherein said antiestrogen having a triphenylethylene base structure has more than one side chain.

8. The method of treating dementia according to claim 6, wherein said composition is administered to the human patient in an amount of about between 5 and 100 mg per day.

9. The method of treating dementia according to claim 6, wherein said composition is administered to the human patient in an amount of about between 20 and 60 mg per day.

10. The method of treating dementia according to claim 6, wherein said composition is administered to the human patient in an amount of about 40 mg per day.

11. The method of treating dementia according to claim 6, where the period for administration is about between 3 months and 24 months.

12. A method of treating dementia in a human patient, the method including the steps of:

forming a pharmaceutical composition containing an antiestrogenically effective amount of an antiestrogen, said antiestrogen having a structure according to the formula

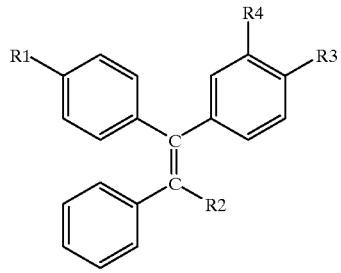

wherein R$_1$ is selected from the group consisting of

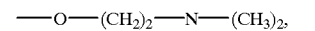

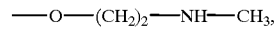

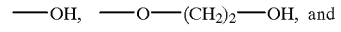

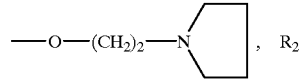

being selected from the group consisting of —CH$_2$—CH$_3$, —C≡N, and —CH$_2$ CH$_2$—Cl, and the remaining R-groups being selected from the group consisting of —H or —I; and administering an amount of said pharmaceutical composition to the human patient in sufficient quantity so as to be effective in the treatment of dementia.

13. The method of treating dementia according to claim 12, wherein said composition is administered to the human patient in an amount of about between 5 and 100 mg per day.

14. The method of treating dementia according to claim 12, wherein said composition is administered to the human patient in an amount of about between 20 and 60 mg per day.

15. The method of treating dementia according to claim 12, wherein said composition is administered to the human patient in an amount of about 40 mg per day.

16. The method of treating dementia according to claim 12, wherein said composition is administered to the human patient in an amount of about 60 mg per day.

17. The method of treating dementia according to claim 12, wherein the period for administration is between about 3 months and 24 months.

* * * * *

UNITED STATES PATENT AND TRADEMARK OFFICE
CERTIFICATE OF CORRECTION

PATENT NO. : 6,232,350 B1
DATED : May 15, 2001
INVENTOR(S) : Denecke

It is certified that error appears in the above-identified patent and that said Letters Patent is hereby corrected as shown below:

<u>Title page,</u>
ABSTRACT, "close" should be -- dose --.

<u>Column 2,</u>
Line 8, delete "the" after "are".
Line 9, delete ",".
Line 14, remove ",".
Lines 57-59, delete "By - channels".

<u>Column 8,</u>
Line 21, delete "Change sin" and insert -- changes in --.
Line 33, delete "rate" and insert -- rat --.

<u>Column 9,</u>
Line 21, remove "factory" and insert -- factor --.
Line 47, "bessel" should be -- vessel --.

<u>Column 10,</u>
Line 40, "extend" should be -- extent --.
Line 42, "sec" should be -- sex --.
Line 66, "nuclear" should be -- unclear --.

<u>Column 11,</u>
Line 39, "though" should be -- thought --.
Line 50, "decreased" should be -- decrease --.
Line 56, delete "reduce din" and insert -- reduced --.

Signed and Sealed this

Eighth Day of January, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,232,350 B1
DATED : May 15, 2001
INVENTOR(S) : Rainer Denecke

It is certified that error appears in the above-identified patent and that said Letters Patent is hereby corrected as shown below:

Column 1,
Line 3, "DIMENTIA" should read -- DEMENTIA --.

Column 2,
Line 38, "neutrons" should read -- neurons --.

Column 4,
Table, in the last line of the table, "$(CH_2)_3$" should read -- $(CH_2)_2$ --.

Column 8,
Line 27, "extend" should read -- extent --.
Line 33, "tamoxifen" should read -- droloxifene --.

Column 10,
Line 41, "form" should read -- from --.
Line 59, "regiment" should read -- regimen --.

Column 11,
Line 26, "degration" should read -- degradation --.
Line 37, "tested" should read -- treated --.

Column 12,
Line 22, "regiment" should read -- regimen --.

Column 13,
Line 14, change "C=N" to -- C≡N --.

UNITED STATES PATENT AND TRADEMARK OFFICE
CERTIFICATE OF CORRECTION

PATENT NO.   : 6,232,350 B1
DATED        : May 15, 2001
INVENTOR(S)  : Rainer Denecke It is certified that error appears in the above-identified patent and that said Letters Patent is hereby corrected as shown below:

<u>Column 14,</u>
Line 19, change "C=N" to -- C≡N --.

Signed and Sealed this

First Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,232,350 B1
DATED : May 15, 2001
INVENTOR(S) : Rainer Denecke

It is certified that error appears in the above-identified patent and that said Letters Patent is hereby corrected as shown below:

Column 1,
Line 3, "DIMENTIA" should read -- DEMENTIA --.

Column 2,
Line 38, "neutrons" should read -- neurons --.

Column 4,
Table, in the last line of the table, "$(CH_2)_3$" should read -- $(CH_2)_2$ --.

Column 8,
Line 27, "extend" should read -- extent --.
Line 33, "tamoxifen" should read -- droloxifene --.

Column 10,
Line 41, "form" should read -- from --.
Line 59, "regiment" should read -- regimen --.

Column 11,
Line 26, "degration" should read -- degradation --.
Line 37, "tested" should read -- treated --.

Column 12,
Line 22, "regiment" should read -- regimen --.

Column 13,
Line 8, change "C=N" to -- C≡N --.

UNITED STATES PATENT AND TRADEMARK OFFICE
CERTIFICATE OF CORRECTION

PATENT NO.   : 6,232,350 B1
DATED        : May 15, 2001
INVENTOR(S)  : Rainer Denecke It is certified that error appears in the above-identified patent and that said Letters Patent is hereby corrected as shown below:

<u>Column 14,</u>
Line 32, change "C=N" to -- C≡N --.

This certificate supersedes Certificate of Correction issued April 1, 2003.

Signed and Sealed this

Thirtieth Day of December, 2003

JAMES E. ROGAN
*Director of the United States Patent and Trademark Office*